US010130938B2

(12) United States Patent
Bai et al.

(10) Patent No.: US 10,130,938 B2
(45) Date of Patent: Nov. 20, 2018

(54) HYDROGENATION CATALYST, ITS METHOD OF PREPARATION AND USE

(71) Applicant: EXXONMOBIL CHEMICAL PATENTS INC., Baytown, TX (US)

(72) Inventors: Chuansheng Bai, Phillipsburg, NJ (US); Jean W. Beeckman, Columbia, MD (US); Hans K. T. Goris, Zaventem (BE); Adrienne J. Thornburg, Columbus, OH (US); Natalie A. Fassbender, Nazareth, PA (US); Sabato Miseo, Pittstown, NJ (US); Stuart L. Soled, Pittstown, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 90 days.

(21) Appl. No.: 14/916,735

(22) PCT Filed: Sep. 2, 2014

(86) PCT No.: PCT/US2014/053679
§ 371 (c)(1),
(2) Date: Mar. 4, 2016

(87) PCT Pub. No.: WO2015/057313
PCT Pub. Date: Apr. 23, 2015

(65) Prior Publication Data
US 2016/0199814 A1 Jul. 14, 2016

Related U.S. Application Data

(60) Provisional application No. 61/892,557, filed on Oct. 18, 2013.

(30) Foreign Application Priority Data

Dec. 17, 2013 (EP) .................................... 13197589

(51) Int. Cl.
| C07C 69/74 | (2006.01) |
| B01J 23/42 | (2006.01) |
| B01J 21/08 | (2006.01) |
| B01J 37/02 | (2006.01) |
| B01J 37/08 | (2006.01) |
| B01J 37/10 | (2006.01) |
| B01J 37/18 | (2006.01) |
| B01J 23/44 | (2006.01) |
| B01J 23/46 | (2006.01) |
| B01J 35/00 | (2006.01) |
| B01J 35/10 | (2006.01) |
| C07C 67/303 | (2006.01) |
| B01J 27/24 | (2006.01) |

(52) U.S. Cl.
CPC ............... *B01J 23/42* (2013.01); *B01J 21/08* (2013.01); *B01J 23/44* (2013.01); *B01J 23/462* (2013.01); *B01J 23/464* (2013.01); *B01J 35/002* (2013.01); *B01J 35/1061* (2013.01); *B01J 37/0203* (2013.01); *B01J 37/0207* (2013.01); *B01J 37/0209* (2013.01); *B01J 37/0242* (2013.01); *B01J 37/0244* (2013.01); *B01J 37/08* (2013.01); *B01J 37/10* (2013.01); *B01J 37/18* (2013.01); *C07C 67/303* (2013.01); B01J 27/24 (2013.01); B01J 2531/821 (2013.01); B01J 2540/62 (2013.01); C07C 2601/14 (2017.05)

(58) Field of Classification Search
None
See application file for complete search history.

(56) References Cited

U.S. PATENT DOCUMENTS

| 4,495,062 | A | * | 1/1985 | Hensley, Jr. ............. B01J 21/02 208/111.2 |
| 4,628,129 | A | | 12/1986 | Bartley |
| 5,334,779 | A | | 8/1994 | Kuo |
| 5,936,126 | A | | 8/1999 | Rühl et al. |
| 2002/0019559 | A1 | | 2/2002 | Brunner et al. |
| 2009/0299109 | A1 | | 12/2009 | Gruber et al. |
| 2011/0082311 | A1 | | 4/2011 | Soled et al. |
| 2012/0184430 | A1 | | 7/2012 | Lee et al. |
| 2012/0296111 | A1 | | 11/2012 | Königsmann et al. |

FOREIGN PATENT DOCUMENTS

| WO | 2004/045767 | 6/2004 |
| WO | 2004/046076 | 6/2004 |
| WO | 2004/046078 | 6/2004 |
| WO | 2012/152821 | 11/2012 |

OTHER PUBLICATIONS

Fang et al. Environ. Sci. Technol. 2007, 41, 3758-3762.*

* cited by examiner

*Primary Examiner* — Ana Z Muresan
(74) *Attorney, Agent, or Firm* — Darryl M. Tyus

(57) ABSTRACT

A method of producing a hydrogenation catalyst, for example, a phthalate hydrogenation catalyst, comprising contacting a silica support having a medium pore size of at least about 10 nm with an acid to produce a treated silica support, and depositing a noble metal, preferably ruthenium, on the treated silica support to produce a noble metal-containing silica support, and optionally contacting the noble metal-containing silica support with a chelating agent to form the hydrogenation catalyst; a hydrogenation catalyst prepared by that method; and a method of hydrogenating unsaturated hydrocarbons, such as, phthalates, in which an unsaturated hydrocarbon is contacted with hydrogen gas in the presence of the hydrogenation catalyst of the invention.

14 Claims, No Drawings

HYDROGENATION CATALYST, ITS METHOD OF PREPARATION AND USE

CROSS REFERENCE TO RELATED APPLICATIONS

This application is a National Stage Application of International Application No. PCT/US2014/053679 filed Sep. 2, 2014, which claims priority to U.S. Provisional Application Ser. No. 61/892,557 filed Oct. 18, 2013, and European Application No. 13197589.8, filed Dec. 17, 2013, the disclosures of each are fully incorporated herein by reference in their entireties.

FIELD OF THE INVENTION

The present invention relates to hydrogenation catalysts, in particular to methods for the preparation of noble metal catalysts, such as ruthenium (Ru) catalysts, for use in the hydrogenation of phthalates.

BACKGROUND

Plasticizers are incorporated into resins to increase their flexibility, workability, and dispensability. Phthalates, especially, the high molecular weight phthalates (HMWP), are used as plasticizers in PVC. Alternatives to phthalates are desirable due to environmental, legislative and regulatory concerns. In particular, the uses of phthalates as plasticizers are under severe pressure. Hydrogenation of phthalates produces 1,2-cyclohexyl dicarboxylates, hereinafter also referred to as cyclohexanoates, which can also be used as plasticizers.

Previous research showed that catalysts consisting of Ru supported on alumina ($Al_2O_3$) with low surface areas are active for the hydrogenation of phthalate to cyclohexanoates. U.S. Pat. No. 5,936,126 (BASF) discloses the hydrogenation of phthalates to cyclohexyl dicarboxylates using catalysts consisting of Ru supported on low surface area alumina at 80 to 120° C. and under 10-20 MPa (100-200 atmospheres) pressure. US 2002/0019559 (BASF) discloses a catalyst for hydrogenation of phthalates comprising ruthenium deposited on an alumina support material that comprises macropores of greater than 50 nm in diameter.

It has also recently been discovered that materials consisting of Ru supported on a silica ($SiO_2$) support with "remnant structure" produced by deposition of an organic ruthenium compound on a silica support to form an organic ruthenium complex on or in the support, followed by decomposition of the complex, have much higher activities and stabilities in the phthalate hydrogenation than reported Ru/$Al_2O_3$ catalysts. WO 2004/046076, WO 2004/045767 and WO 2004/046078 (ExxonMobil) disclose catalysts of Ru on silica supports prepared with the remnant structures. US 2012/0296111 (BASF) discloses an eggshell catalyst for hydrogenating carbocyclic aromatic compounds, such as phthalates, comprising a noble metal, such as ruthenium, deposited on a silica support material in which at least 90% of the pores present have a pore diameter of 6 to 12 nm. The catalysts may be prepared by depositing ruthenium acetate on the silica support and then reducing.

Large pore extruded silica is a commercially available catalyst support. US 2010/0133148 (ExxonMobil) discloses a hydrodesulfurization catalyst comprising cobalt and molybdenum salts impregnated on large pore silica supports. The large pore support is prepared by steam-treating a silica support material. The catalyst is prepared by impregnating the silica support with a solution containing the metal ions, an organic additive, which is an alcohol or aminoalcohol, an organic acid and an inorganic acid. US 2012/0184430 (Samsung) discloses the synthesis of a metal oxide support material, such as mesoporous silica, that has surface hydroxyl groups, including hydroxyl groups within its pores, and the preparation of a carbon dioxide reforming catalyst comprising a metal deposited onto that support material. However, the use of large pore silica as an effective support for ruthenium in a phthalate hydrogenation catalyst has not previously been achieved.

It has been found that large pore silica supports can facilitate the mass transfer of large molecules of phthalate during catalytic reactions, which can be beneficial to the catalyst activity for phthalate hydrogenation to cyclohexanoates. However, in order to have large pores and high crush strength, the silica support is steam-treated at high temperature. During the high temperature steaming treatments, the improved extrudate crush strength and large porosity are accompanied by decreases of hydroxyl group concentration and surface area of the steamed silica support. As a consequence, known strong and large pore silica supports usually have low surface areas and low concentration of Si—OH hydroxyl groups due to high temperature steaming. Si—OH hydroxyl groups are required for complexion to noble metals, such as ruthenium. Therefore, commercially available large pore silica is not particularly suitable for use as ruthenium supports for phthalate hydrogenation catalysts.

There remains a need for metal oxide-supported noble metal catalysts which are highly active in phthalate hydrogenation. In particular, there remains a need for a metal oxide support that can both facilitate the mass transfer of large molecules of phthalate during catalytic reactions and which has a high concentration of Si—OH hydroxyl groups for complexion to noble metals, such as ruthenium.

SUMMARY OF THE INVENTION

In a first aspect, the invention provides a method for the synthesis of a silica-supported noble metal hydrogenation catalyst, in particular a silica-supported ruthenium hydrogenation catalyst, in which the surface of the silica support is treated with an acid prior to being contacted with a noble metal compound, for instance a ruthenium compound. In one embodiment, the invention provides a method for the preparation of a silica-supported noble metal (e.g., ruthenium) catalyst comprising the steps of: (a) contacting a silica support with an acid to produce a treated silica support; and (b) depositing a noble metal (e.g., ruthenium) on the treated silica support produced in step (a), such as, by contacting the treated silica support produced in step (a) with a solution comprising said noble metal (e.g., ruthenium) and an optional chelating agent to produce a noble metal-containing silica support. The noble metal-containing silica support obtained in step (b) may be used as such as a hydrogenation catalyst or it may be subjected to further processing steps before being used as a catalyst. The silica support is optionally calcined after contact with the acid (i.e., after step (a)) and/or optionally calcined after deposition of the noble metal (i.e., after step (b)). The catalyst obtained by this process is suitable for use in the hydrogenation of unsaturated hydrocarbon compounds, especially aromatic compounds, such as phthalates. The method may further comprise the step of steam-treating a silica to produce the silica support used in step (a). The silica support used in step (a) is preferably a large pore silica support, for example, produced by steam-treating. The silica support may, for example have a median pore size of at least 10 nm, especially at least 20 nm. Additionally or alternatively the silica support may have a high crush strength, for example a crush strength of at least 800 g/mm, in particular at least 1000 g/mm. The acid used in step (a) is preferably an aqueous solution of a strong acid, such as nitric acid ($HNO_3$). The making of the treated silica support optionally further comprises drying and/or calcining the silica support subsequent to the contacting with acid. The method optionally further comprises drying and/or calcining the noble metal-containing silica support. Preferably, the method comprises the step (c) of calcining the treated silica support after deposition of the noble metal, for example, subsequent to the contacting of the treated silica support with a solution comprising the noble metal and an optional chelating agent. The method optionally further comprises the step (d) of activating the catalyst by contacting the noble metal-containing silica support obtained in step (b) or (c) with hydrogen gas.

In a second aspect, the invention provides a silica-supported noble metal hydrogenation catalyst comprising a noble metal, preferably ruthenium, dispersed on a silica support having a median pore size of at least 10 nm, especially at least 20 nm. Advantageously the catalyst of the second aspect of the invention has a hydrogen to noble metal chemisorption ratio of at least 0.50, especially at least 0.60. Advantageously, the catalyst of the second aspect of the invention has a crush strength of at least 800 g/mm, in particular at least 1000 g/mm. The silica-supported noble metal, preferably ruthenium, hydrogenation catalyst of the second aspect of the invention may, for example, be prepared by the method of the first aspect of the invention. The hydrogenation catalysts of the invention are suitable for the catalysis of hydrogenation processes, for example, processes in which unsaturated hydrocarbons, such as aromatic compounds, are hydrogenated using hydrogen gas, especially for use in catalyzing phthalate hydrogenation.

In a third aspect, the invention provides a method of hydrogenating unsaturated hydrocarbons, especially phthalates, comprising the step of contacting an unsaturated hydrocarbon with a catalyst of the second aspect of the invention or a catalyst obtainable or obtained by the method of the first aspect of the invention, for example, in the presence of hydrogen gas.

In a fourth aspect, the invention provides a method of increasing the concentration of hydroxyl (Si—OH) groups on the surface of a silica support having a median pore size of at least 10 nm, especially at least 20 nm, comprising the step of treating the silica support with an acid. For example, the invention provides a method of increasing, for example, repopulating, the hydroxyl group concentration of a silica support following steam treatment, the method comprising the step of treating the silica support with an acid, such as nitric acid.

In a fifth aspect, the invention provides a silica support having a median pore size of at least 10 nm, especially at least 20 nm, and a hydroxyl group concentration sufficient to provide a catalyst having a hydrogen to noble metal chemisorption ratio of at least 0.5, especially at least 0.6, following deposition of the noble metal on the catalyst surface. Advantageously, the silica support of the fifth aspect of the invention, or prepared by the fourth aspect of the invention, has a crush strength of at least 800 g/mm, in particular at least 1000 g/mm. The silica support of the fifth aspect of the invention may, for example, be prepared by increasing the hydroxyl (Si—OH) group concentration of a large pore silica support, such as a commercially available large pore silica support or a silica support which has been steam-treated, in accordance with the method of the fourth aspect of the invention.

It has been found that treating silica supports with acid, especially nitric acid, improves the dispersion of noble metals, for instance ruthenium, onto the silica support. Without wishing to be bound by any theory, it is believed that treating a silica support that has been modified by high temperature steaming with acid, repopulates the hydroxyl groups on silica surface increasing the concentrations of hydroxyl groups for noble metal anchoring and restores the surface areas which were lost during the high temperature steaming. It has also been found that following acid treatment of the silica support, the properties of high crush strength and large porosity of a steam-treated silica are preserved. Hydrogen chemisorption experiments have demonstrated that treatment of a silica support with acid prior to contacting the support with noble metal compounds results in a catalyst with substantially improved noble metal dispersion on the silica surface. To form silica-supported noble metal hydrogenation catalysts of the invention, the noble metal is preferably dispersed on a silica support with a chelation aid. Suitable chelation aids include amino alcohols, such as triethanolamine (TEA). For instance, TEA and Ru ions form complexes of Ru-TEA, which are anchored to the silica surface via the interactions with hydroxyl groups of an extruded silica support. The hydroxyl groups of the silica support are the anchoring points for noble metal dispersions.

DETAILED DESCRIPTION OF THE INVENTION

The noble metal present in the hydrogenation catalyst of the present invention is typically selected from the group consisting of ruthenium, rhodium, palladium, platinum and mixtures thereof, preferably ruthenium, most preferably ruthenium as the sole active metal.

The silica support used in step (a) is a large pore silica. Large pore silicas are commercially available as a catalyst support. Large pore silicas typically have the property of high crush strength as well as large pore sizes and are usually produced by high temperature steaming. Silica supports used in the present invention typically have a median pore size of at least about 10 nm, for example, at least about 15 nm, especially at least about 20 nm, such as at least about 25 nm. The silica support typically has a median pore size of no more than about 300 nm, for example, no more than about 200 nm, especially no more than about 150 nm. For example, the silica support may have a median pore size of from about 10 to about 100 nm, such as from about 15 nm to about 80 nm. The median pore size may be determined by mercury porosimetry, for example, according to ASTM D4284-12. The pores may be approximately spherical or an irregular shape and the pore size is the largest dimension of the pore, which is also known in the art as to as the "pore diameter" or "pore axis". Typically the large pore silica has a crush strength of at least 893 g/mm (50 lb/in), for example, at least 1072 g/mm (60 lb/in), preferably at least 1251 g/mm (70 lb/in), especially at least 1430 g/mm (80 lb/in). Crush strength is measured using the standard test method for single pellet crush strength of formed catalyst shapes set out in ASTM D4179-01. Suitable silica supports having the properties described above are described in U.S. Pat. No. 8,216,958 (ExxonMobil), the disclosure of which is incorporated herein by reference.

The silica support used in the method of the invention can have any suitable shape or form. Preferably, the silica support is in the form of tablets, pellets, extrudates, spheres, and the like and combinations thereof. The extrudates may be of any cross section, for example, circular to form cylinders or tubes as well as trilobe or quadrulobe to form prisms. The silica support is typically a silica extrudate or a silica bead, preferably a silica bead.

If the silica support particles used in the method of the first aspect of the present invention are in the form of silica beads, spheres, tablets or pellets, the particle size distribution of said silica support may be determined by dry sieve analysis according to ASTM C136-96a. Said particle size distribution may be characterized by its D10, D50 and D90 values where D50 corresponds to the size at which 50 wt % of the sample is smaller and 50 wt % of the sample is larger. In the present invention, D50 is used to characterize the silica support average particle size or average diameter. The width or span of the particle size distribution is calculated as (D90-D10)/D50. The particle size distribution of a population of particles used in the present invention is typically relatively narrow, for instance with a span equal to or lower than 2, preferably equal to or lower than 1.5, more preferably equal to or lower than 1, in particular equal to or lower than 0.5 such as about 0.2.

If the silica support particles used in the method of the first aspect of the present invention are the form of extrudates, i.e., in the form of elongated shapes having a substantially constant cross section which corresponds to the hole of the extrusion die, the silica support particles may be characterized by an average length, an average diameter and an average aspect ratio. According to the present invention, the length of an extrudate corresponds to the extruded length of said extrudates, the diameter of an extrudate corresponds to the outside diameter of said extrudate cross section, i.e., the diameter of the smallest circle circumscribing the cross section, and the aspect ratio of an extrudate corresponds to the ratio of its length on its diameter. Thus, for example, for a cylindrical extrudate, the diameter of the particle corresponds to the diameter of the disc cross section. For an extrudate having an elliptic cross section, the diameter of the particle is the major axis of the ellipse, i.e., the line segment that runs through the center and both foci, with ends at the widest points of the extruded elliptical cross section. For a symmetric quadrulobe extrudate, the diameter is the highest dimension of the quadrulobe section, i.e., the longest distance, in a straight line between two points on the quadrulobe cross section and its center. The diameter of an extrudate is substantially constant, as the cross section of the extrudate is dictated by the size of the hole in the extrusion die. The average length, average diameter, and average aspect ratio of the extrudate silica support particles of the present invention may be determined by optical scanner imaging using ALIAS Image Analysis System (Cascade Data System). The sample size is typically of 150 to 250 particles, without sample preparation per se. The average length and average diameter are the numerical averages (arithmetic means) of the measured individual lengths and diameters while the aspect ratio is the fraction of said average length on said average diameter. The average length of the extrudate silica support particles used in the method of the first aspect of the invention can vary widely and is not critical. In the present invention, the average length to diameter aspect ratio of said extrudate silica support particles is usually at least 1, most often higher than 1, typically at least about 2, in particular at least about 2.5, for example, at least about 3. Said average aspect ratio is usually at most about 10, typically at most about 8, for instance at most about 5.

The average diameter of the silica support particles used in the method of the first aspect of the invention, whether beads, spheres, tablets or pellets, extrudates or other forms, is generally in the range of from about 0.8 mm to about 10 millimeters (mm), preferably in the range of from about 1.0 mm to about 5 mm, and more preferably in the range of from about 1.2 mm to about 3 mm, such as from about 1.3 mm to about 2 mm. Preferably, the average diameter of the particles is no more than about 2.4 mm, for example, no more than about 2.2 mm, especially no more than about 2.0 mm. In some embodiments, the silica support consists of particles having an average diameter of less than about 2.0 mm, for example, no more than about 1.8 mm, especially no more than about 1.7 mm. Typically, the particles have an average diameter of at least 0.7 mm. Preferably, the silica support consists of particles having an average diameter of from about 0.8 mm to about 2.2 mm, especially from about 1.0 mm to about 2.0 mm, for example from about 1.2 mm to about 1.8 mm. The catalyst of the second aspect of the invention typically consists of particles of substantially the same size as the silica support listed above. For example, a catalyst of the second aspect of the invention based on silica support particles in the form of beads, spheres, tablets, pellets or extrudates, preferably consists of particles having an average diameter of from about 0.7 mm to about 2.4 mm, especially from about 0.8 mm to about 2.2 mm, for example, from about 1.0 mm to about 2.0 mm. The average diameter of the particles of support or catalyst may, for example, be measured by dry sieve analysis and/or optical scanner imaging as appropriate.

The silica support used in the method of the invention has advantageously been steam treated. The method of the first or third aspects of the invention optionally comprises the additional step of heating a silica, for example, a silica extrudate, in the presence of steam prior to step (a). The silica material is optionally heated to a temperature of at least 400° C., such as at least about 450° C., for example, a temperature in the range of from about 500° C. to about 800° C. in the presence of steam, for example, in an atmosphere comprising at least 5 wt % steam, especially at least 10 wt % steam. The step of steam treating a silica material advantageously increases the crush strength and/or the pore size of the silica material and can therefore be used to prepare a silica support having a large pore size, e.g., a pore size of 10 nm or greater, especially 15 nm or greater, and a high crush strength, e.g., a crush strength of 800 g/mm or greater, especially 1000 g/mm or greater.

The silica support preferably has a silica content of at least 60 wt %, for example, at least 80 wt %. In addition to silica, the support may, for example, also comprise alumina, however alumina is preferably a minor component. Accordingly, the silica support preferably comprises no more than 40 wt % alumina, for example, no more than 20 wt % alumina, especially no more than 10 wt % alumina.

The silica support used in the methods of the invention typically has a pore volume of at least about 0.2 ml/g, for example, at least about 0.5 ml/g, especially at least about 0.6 ml/g. The silica support typically has a pore volume of no more than about 3.0 ml/g, for example, no more than about 2.0 ml/g, especially no more than about 1.5 ml/g. The pore volume may be determined by mercury porosimetry, for example, according to ASTM D4284-12. A large pore silica support for use in preparing the treated silica support used in the present invention generally has a surface area, measured by the Brunauer, Emmett, Teller (BET) method, ASTM D1993, in the range of from about 20 m$^2$/g to about 400 m$^2$/g, preferably in the range of from about 40 m$^2$/g to about 300 m$^2$/g, and more preferably in the range of from about 50 m$^2$/g to about 200 m$^2$/g.

The acid used in step (a) is any suitable acid which is capable of repopulating hydroxyl groups on the surface of silica. Suitable acids include inorganic acids, such as, nitric acid ($HNO_3$); sulfuric acid ($H_2SO_4$), optionally with hydrogen peroxide ($H_2O_2$); hydrofluoric acid (HF); and hydrochloric acid (HCl). Nitric acid is especially preferred. Typically the acid is in the form of an aqueous solution and the silica is washed with the acidic solution in step (a) of the first or third aspects of the invention. Typically the aqueous solution has a pH of from about −1.5 to +4.0, such as from about −1.0 to about +3.0 or from about 0.0 to about +3.0. An acidic solution with a pH in those ranges, i.e., a pH of around 0, for example, an approximately 1 N solution of a strong acid, such as nitric acid, has been found to be effective in repopulating the hydroxyl groups on a silica support that has been steam-treated. Typically, the aqueous solution is a solution of a strong acid, i.e., an acid which fully dissociates in water. Typically, the acidic solution is a 0.2 N to a 6 N solution, for example, a 0.4 N to 5 N solution, such as a 0.5 N to 3 N solution, of a strong acid in water. In step (a), the silica support can be contacted with the acid at any suitable temperature and pressure, for instance at room temperature and atmospheric pressure.

After contacting the silica support with an acid, the acid treated silica support is optionally subjected to a washing and/or drying step. The washing is typically done with water. The drying step maybe carried out at a temperature generally in the range of from about 40° C. to about 180° C., preferably in the range of from about 60° C. to about 160° C., and more preferably in the range of from about 80° C. to about 150° C. The drying step may be performed under reduced pressure or under atmospheric pressure, in an inert atmosphere or in air; conveniently, it can be performed in air and under atmospheric pressure. The drying can also be promoted by passing a gas stream over or through the material to be dried, for example, air or nitrogen. The drying time depends upon the desired degree of drying and the drying conditions and is preferably in the range of from 1 hour to 30 hours, preferably from 2 hours to 10 hours. Further optionally, and alternatively or additionally to the drying step, the preparation of a treated silica support may comprise calcining under a calcining condition, such as exposure to a high temperature, for example, in the range of from about 250° C. to about 1000° C., preferably in the range of from about 300° C. to about 900° C., and more preferably in the range of from about 400° C. to about 700° C. The calcination step preferably occurs in the presence of oxygen, for example, in air. During calcining, substantially all volatile matter (e.g., water and carbonaceous materials) is removed. Advantageously, the support is subject to calcination prior to deposition of the noble metal in step (b). The step of contacting a silica support with an acid together with optional drying and calcination steps are collectively referred to as a "treatment step" that produces a treated silica support.

Advantageously, the acid treatment step (a) increases the concentration of hydroxyl groups on the silica support by at least 1 Si—OH group by per nm$^2$, for example, by at least 1.5 Si—OH group per nm$^2$. Silica Si—OH concentrations can, for example, be measured by reacting the active hydrogen of the hydroxyl groups of a known quantity of silica with a $C_2H_5MgBr$ ethyl magnesium bromide Grignard reagent to produce ethane $C_2H_6$. The volume of ethane evolved can be used to calculate active hydrogen of OH groups of the silica support. Alternatively, a calibration curve of standard silica materials with known OH concentrations can be made using Fourier Transform Infrared Spectroscopy (FTIR) and then the FTIR of a silica with unknown OH concentrations can be compared against the calibration curve. The treated silica support typically has a hydroxyl group concentration of at least about 3.5 OH/nm$^2$, for example, at least about 3.8 OH/nm$^2$, especially at least about 4.0 OH/nm$^2$. Advantageously, the step (a) of treating the silica support increases the concentration of hydroxyl groups on the silica support such that the maximum hydrogen to noble metal chemisorption ratio (hereinafter also referred to as H/noble metal chemisorption ratio) that can be achieved following noble metal deposition is increased by at least 0.1 compared to the untreated large pore silica support. As discussed in more detail below, the hydrogen to noble metal chemisorption ratio is an indication of the level of dispersion of the metal on the support and an indication of the availability of the metal atoms as catalytic sites. High hydrogen to noble metal chemisorption ratios are thus indicative of higher catalytic activity. Advantageously, the step (a) of treating the silica support increases the concentration of hydroxyl groups on the silica support such that a hydrogen to noble metal chemisorption ratio in excess of 0.5 can be achieved after deposition of noble metal, preferably ruthenium, onto the silica support. Usually, the surface area of the silica support after treatment in step (a), measured by the Brunauer, Emmett, Teller (BET) method, ASTM D1993, does not substantially decrease, i.e., does not decrease by more than 10%, preferably does not decrease by more than 5%, more preferably does not decrease by more than 2%. Advantageously, the step (a) of treating the silica support even increases the surface area of the support as measured by the Brunauer, Emmett, Teller (BET) method, ASTM D1993. For example, the treated silica support may have a BET surface area of at least about 10 m$^2$/g, preferably at least about 20 m$^2$/g, especially at least about 25 m$^2$/g greater than the untreated large pore silica support. In some embodiments, the BET surface area is increased by at least about 30 m$^2$/g in step (a). Advantageously, the treated large pore silica support has a surface area, measured by the Brunauer, Emmett, Teller (BET) method, ASTM D1993, of at least about 30 m$^2$/g, preferably at least about 40 m$^2$/g, and more preferably at least about 45 m$^2$/g. In some embodiments the treated silica support produced in step (a) has a surface area, measured by BET method of at least about 50 m$^2$/g. Typically, the surface area as measured by the BET method is 300 m$^2$/g or less, for example, 200 m$^2$/g or less, such as 150 m$^2$/g or less.

The noble metal is typically deposited on the treated silica support by contacting the treated silica support with a noble metal-containing liquid, typically with a precursor compound of the noble metal. Suitable precursor compounds are noble metal compounds which can be converted into metallic compounds. Examples of suitable contacting manners include, but are not limited to, impregnation, mixing, immersion, and the like. Generally, depositing a noble metal on the treated silica support comprises an impregnation technique. Generally, the treated silica support is impregnated with a noble metal precursor dissolved in an aqueous solution such as deionized water, by immersing the silica support in the solution of noble metal precursor, for example, by incipient wetness impregnation in which the pores of the treated silica support are filled with the solution. The treated silica support can also be sprayed with an impregnating solution containing a dissolved noble metal precursor component. The amount of noble metal precursor utilized in the method of the first aspect of the present invention is such as to provide a concentration of said noble metal on the silica support that is suitable to catalyze hydrogenation reactions, for example, the hydrogenation of phthalates into cyclohexanoates. Typically, the concentration of noble metal in a catalyst of the second aspect of the present invention is in the range of from about 0.1 wt % to about 5 wt % based on the total weight of the catalyst composition, preferably in the range of from about 0.1 wt % to about 2 wt %, and more preferably in the range of from about 0.2 wt % to about 1 wt %, based on the total weight of the catalyst composition. Generally, the concentration of the noble metal precursor in the impregnating solution is in the range of from about 0.01 Molar (M) to about 1.0 M, preferably in the range of from about 0.01 M to about 0.20 M, and more preferably in the range of from about 0.02 M to about 0.10 M, especially from about 0.03 M to about 0.08 M. Examples of a suitable solvent of the impregnating solution include, but are not limited to, deionized water, an alcohol and combinations thereof.

The noble metal may be deposited on the surface of the treated silica support in any form, including salt forms, organo-metal compounds, metal oxides or complexes comprising noble metal atoms or ions. The noble metal is typically deposited onto the silica support as a salt, for example, in a suitable solvent, such as water or another polar protic solvent, such as $C_1$-$C_4$ alkanols, for instance methanol, ethanol, n-propanol or isopropanol. Suitable noble metal salts include nitrate, nitrosyl nitrate, halide (typically bromide, chloride or iodide) and acetate salts, in particular nitrosyl nitrate. Ruthenium nitrosyl nitrate salts are especially preferred. Alternatively, the noble metal may be deposited onto the treated silica catalyst support by contacting the treated silica catalyst support with noble metal oxide, for instance ruthenium oxide.

Advantageously, the noble metal is deposited on the silica support in the form of a salt and in the presence of a chelating agent, more preferably as a noble metal-chelating agent complex, for example, as a ruthenium-chelating agent complex. The formation of a noble metal-chelating complex typically inhibits undesired interactions among noble metal atoms, thus preventing noble metal particle agglomerations. The chelating agent advantageously acts as a dispersion aid.

The chelating agents for use in the methods of the invention include at least one and in particular from 1 to 6 nitrogen-containing functional groups selected from amine and imine functional groups (i.e., amino and/or imino groups), such as from 1 to 6 secondary or tertiary amine functional groups. Preferably the chelating agent also includes at least one carboxylic acid and/or hydroxyl functional group, preferably from 1 to 6 carboxylic acid and/or hydroxyl functional groups, more preferably from 2 to 6 carboxylic acid and/or hydroxyl functional groups. In a particular embodiment, the chelating agent has from 2 to 20 carbon atoms, for example, from 4 to 15 carbon atoms. Advantageously, the chelating agent comprises at least one carboxylic acid and/or hydroxyl functional group as well as at least one nitrogen-containing functional group selected from amine and imine functional groups (preferably amine functional group), and has from 2 to 20 carbon atoms. Especially suitable chelating agents are amino alcohols and/or amino carboxylic acids comprising 1 to 6 carboxylic acid and/or hydroxyl functional groups, preferably at least 2 carboxylic acid and/or hydroxyl functional groups, more preferably 2 to 6 carboxylic acid and/or hydroxyl functional groups and 1 to 6 nitrogen-containing functional groups selected from amine and imine groups, especially 1 to 6 amine groups, more particularly 1 to 6 secondary or tertiary amine groups, and 2 to 20 carbon atoms, preferably from 2 to 15 carbon atoms, for example, from 2 to 10 carbon atoms. Advantageously, the chelating agent comprises 1 to 6 hydroxyl functional groups, preferably 2 to 6 hydroxyl functional groups, and 1 to 6 amine or imine functional groups, especially 1 to 6 amine functional groups, preferably 1 to 6 secondary or tertiary amine groups, and 2 to 20 carbon atoms, in particular from 2 to 15 carbon atoms, especially 2 to 10 carbon atoms. Suitable chelating agent include those described in U.S. Pat. No. 3,761,428 (Institute Francais du Petrole) (see col. 1, lines 51 to 64) and those described in US 2010/0133148 (ExxonMobil) (see paragraphs [0038] to [0042]), the disclosure of both of which is incorporated herein by reference. Preferred chelating agents for use in the methods of the invention include $C_2$ to $C_{20}$ amino alcohols, including dialkanolamines such as diethanolamine, dialkanoldiamines, and trialkanolamines, for instance triethanolamine (TEA). Other suitable chelating agents are amino carboxylic acids, including polyamino carboxylic acids, amino polycarboxylic acids, such as nitrilotriacetic acid (NTA), and polyamino polycarboxylic acids, such as ethylenediaminetetraacetic acid (EDTA), as well as polyamines, such as guanidine. Preferred chelating agents are TEA and EDTA, with TEA being especially preferred. Chelating agents comprising carboxylic acid and/or hydroxyl functional groups as well as nitrogen-containing functional groups selected from amine and imine functional groups have been found to form complexes with noble metal ions, such as Ru-TEA. Those complexes are advantageously anchored to the silica surface via the interactions with the hydroxyl groups (Si—OH) of the silica support. It has also been found that chelating agents comprising carboxylic acid or hydroxyl functional groups as well as at least one nitrogen-containing functional group selected from amine and imine groups form particularly strong interactions with the hydroxyl groups (Si—OH) of the silica support. Thus, chelating agents comprising amine and/or imine functional groups as well as carboxylic acid and/or hydroxyl functional groups have been found to be the most effective dispersion aids for noble metals. Typically, the noble metal is deposited on the silica support in the presence of an excess of chelating agent, for example, at least 5 molar equivalents of chelating agent, especially at least 10 molar equivalents of chelating agent, such as at least 15 molar equivalents of chelating agent.

After depositing the noble metal on the treated silica support, the resulting noble metal-containing silica support may be subjected to a washing and/or drying step. The washing step typically uses water. This drying step typically includes a temperature generally in the range of from about 20° C. to about 200° C., preferably in the range of from about 50° C. to about 175° C., and more preferably in the range of from about 75° C. to about 150° C. The drying step may be performed under reduced pressure or under atmospheric pressure, in an inert atmosphere or in air, most often in air and under atmospheric pressure. The drying can also be promoted by passing a gas stream over or through the material to be dried, for example, air or nitrogen. The drying time depends upon the desired degree of drying and the drying conditions and is preferably in the range of from 1 hour to 30 hours, preferably from 2 hours to 10 hours.

Further optionally, and alternatively or additionally to the drying step, the noble metal-containing silica support is calcined under a calcining condition, such as exposure to a high temperature, for example, in excess of about 200° C., preferably in excess of about 240° C., and more preferably in excess of about 260° C., for example, from about 200° C. to about 600° C., such as from about 240° C. to about 400° C. During calcining, substantially all volatile matter (e.g., water and carbonaceous materials) is removed. The calcination step is usually conducted in air.

Advantageously a calcination step is performed at least once in the method of the invention, either after contacting the silica support with an acid in step (a), or after depositing the noble metal on the treated silica support in step (b). The calcination step performed after depositing the noble metal on the treated silica support is typically conducted at a lower temperature than that performed after contacting the silica support with an acid. For example, the optional calcination step performed after deposition of the noble metal may be performed at a temperature of at least about 100° C., for example, at least about 200° C. less than the temperature of the calcination step performed prior to deposition of the noble metal on the silica support. The optional calcination step performed after deposition of the noble metal may, for example, be carried out at a temperature of from about 200° C. to about 450° C., for example, from about 240° C. to about 350° C. Preferably, the treated silica support is at least calcined after deposition of the noble metal onto the treated silica support in step (b). In a preferred embodiment of the method of the first aspect of the invention, step (c) is the step of calcining the noble metal-containing silica support.

Advantageously, the noble metal-containing silica support produced following deposition of the noble metal on the treated silica support is subjected to an activation step (d), in which the noble metal-containing silica support is contacted with hydrogen gas. If a calcining step (c) is performed after deposition of the noble metal onto the treated silica support, the activation step (d) is performed after the calcination step. Typically, the noble metal-containing silica support is exposed to an atmosphere comprising at least 60% by volume hydrogen, for example, at least 80% by volume hydrogen, especially at least 95% by volume hydrogen, for example, an atmosphere of essentially 100% hydrogen. Any gas present in addition to hydrogen is preferably an inert gas such as nitrogen. Typically the noble metal-containing silica support is contacted with hydrogen gas at an elevated temperature such as a temperature of at least about 200° C., for example, a temperature of at least about 300° C., especially a temperature of at least about 400° C. For example, the noble metal-containing silica support may be contacted with hydrogen gas at a temperature of from about 300° C. to about 650° C., such as from about 400° C. to about 550° C. Typically the hydrogen pressure is slightly above ambient pressure, such as a pressure of from about 10 kPa gauge to about 100 kPa gauge, such as about 34 kPa gauge (5 psig), i.e., around 136 kPa absolute pressure. Typically, the noble metal-containing silica support may be contacted with hydrogen gas for at least about 1 hour, such as for at least about 2 hours. Preferably, the noble metal-containing silica support is contacted with hydrogen gas for no more than about 5 hours. Contacting of the noble metal-containing silica support with hydrogen gas for about 2.5 hours has been found to be sufficient to fully activate the catalyst.

The activation step (d) may optionally be followed by a passivation step (e). Such a passivation step (e) can for instance be conducted by treating the catalyst briefly in an oxygen-containing gas, for example, air, but preferably with an inert gas mixture comprising from 1 to 10 volume percent of oxygen. It is also possible to use $CO_2$ or $CO_2/O_2$ mixtures. The passivation step may for instance be conducted at room temperature under atmospheric pressure for a few hours.

Advantageously, the catalyst of the second aspect of the invention and/or the catalyst produced by the method of the first aspect of the invention, has a hydrogen to noble metal chemisorption ratio, H/noble metal chemisorption ratio, preferably H/Ru chemisorption ratio, of at least about 0.50, especially at least about 0.60, preferably at least about 0.65. The H/noble metal chemisorption ratio is the ratio of hydrogen atoms absorbed on the catalyst for each noble metal atom and thus is a measure of the dispersion of the noble metal on the catalyst. A H/noble metal chemisorption ratio of 1 would indicate that 100% of noble metal atoms are bound to a hydrogen atom after chemisorption of hydrogen and are thus fully dispersed, such that each noble metal atom is accessible for hydrogen binding. A H/noble metal chemisorption ratio of 0.5 indicates that only 50% of the noble metal atoms are able to bind to hydrogen, the remainder being inaccessible. Suitable conventional volumetric chemisorption techniques which can be employed to measure hydrogen chemisorption of the catalysts of the invention are discussed in Structure of Metallic Catalysts, J. R. Anderson, Academic Press, 1975, chapter 6. The hydrogen to noble metal chemisorption ratio can, for example, be calculated by reduction of a sample of silica-supported noble metal catalyst that contains a known quantity of noble metal with hydrogen and determining the quantity of hydrogen absorbed onto the catalyst, for example, by extrapolation of the isothermal profile to zero hydrogen pressure, after reduction of the sample at 200° C. in hydrogen for 30 minutes.

Advantageously, the catalyst produced in the method of the invention substantially retains the pore size of the silica support used in its preparation. Preferably, the catalyst of the second aspect of the invention and/or the catalyst produced in the method of the first aspect of the invention has a median pore size of at least about 10 nm, for example, at least about 15 nm, especially at least about 20 nm, such as at least about 25 nm. Advantageously, the catalyst produced in the method of the first aspect of the invention has a median pore size at least about 80%, for example, at least about 85%, especially at least about 90%, such as at least about 95% of that of the large pore silica support used in step (a).

The catalyst of the second aspect of the invention or the catalyst produced by the method of the first aspect of the invention is especially suitable as a hydrogenation catalyst, in particular for the hydrogenation of unsaturated hydrocarbons, especially phthalates, for instance, dimethyl phthalate, di-2-propylheptyl phthalate, di-2-ethyl-hexyl phthalate, dioctyl phthalate, or diisononylphthalate.

In one embodiment of the second aspect of the invention, there is provided a silica-supported noble metal catalyst, preferably a silica-supported ruthenium catalyst, wherein the median pore size of the silica support is at least 10 nm, especially at least 20 nm; the catalyst has an hydrogen chemisorption, H/Ru of at least 0.50, especially at least 0.60; and optionally the catalyst has a crush strength of at least 800 g/mm, for example, at least 1000 g/mm.

In one embodiment, the method of the first aspect of the invention is a method of producing a hydrogenation catalyst which comprises the steps of: providing a silica support having a median pore size of at least 10 nm, especially at least 20 nm, for example, by steam-treating a silica extrudate or other silica material; (a) contacting the silica support with an acid, such as an aqueous solution of acid to make a treated silica support; optionally drying and/or calcining the treated silica support obtained in step (a); (b) depositing ruthenium on the treated silica support by contacting the treated silica support with a solution comprising ruthenium and a chelating agent wherein the chelating agent comprises at least one carboxylic acid or hydroxyl functional group as well as at least one nitrogen-containing functional group selected from amine and imine groups, to form a ruthenium-containing silica support; optionally drying the ruthenium-containing silica support; optionally (c) calcining the ruthenium-containing silica support to form a silica-supported ruthenium catalyst; and optionally (d) activating the silica-supported ruthenium catalyst by contacting the silica-supported ruthenium catalyst with hydrogen gas. In further embodiment, the method of the first aspect of the invention is a method of producing a phthalate hydrogenation catalyst which comprises the steps of: providing a silica support having a median pore size of at least 10 nm, especially at least 20 nm, for example, by steam-treating a silica extrudate or other silica material; (a) contacting the silica support with an acid, such as an aqueous solution of acid, especially an aqueous solution of nitric acid, to make a treated silica support; optionally drying and/or calcining the treated silica support obtained in step (a); (b) depositing ruthenium on the treated silica support by contacting the treated silica support with a solution comprising a ruthenium salt and a $C_{2-6}$ amino alcohol chelating agent to form a ruthenium-containing silica support; optionally drying the ruthenium-containing silica support, (c) calcining the ruthenium-containing silica support to form a silica-supported ruthenium catalyst; and optionally (d) activating the silica-supported ruthenium catalyst by contacting the silica-supported ruthenium catalyst with hydrogen gas. The catalyst may, for example, be made by impregnation of an aqueous solution of a ruthenium salt, advantageously ruthenium nitrosyl nitrate, in the presence of TEA onto an acid-treated large pore silica support (median pore size of at least about 10 nm), especially by impregnation of a nitric acid-treated, large pore, silica support with an aqueous solution of ruthenium nitrosyl nitrate-TEA complex.

EXAMPLES OF THE INVENTION

The following examples illustrate the present invention. Numerous modifications and variations are possible and it is to be understood that within the scope of the appended claims, the invention may be practiced otherwise than as specifically described herein.

Commercially available, large pore, RT-235, silica support in the form of cylindrical extrudates having an average diameter of about 1.4 mm (1/18 inch), manufactured by Albemarle, was washed with 1N nitric acid solution. The treated silica support was dried and calcined before the impregnation with a Ru-TEA solution. Then, the Ru-TEA impregnated silica samples were dried and calcined in air. The activation of the catalysts was carried out in a pure hydrogen flow.

Example 1—Silica Support Acid Washing

RT-235 silica support particles were continuously treated with a circulating nitric acid aqueous solution (1N $HNO_3$) at room temperature for 1 hour. The nitric acid solution was then refreshed and circulation was continued for another 1 hour. The nitric acid treated RT-235 silica support sample was washed with deionized water three times, then it was dried at 120° C. (250° F.) overnight in air. The treated silica support was calcined in air at 540° C. (1000° F.) for 6 hours with a ramping rate of about 2.8° C./min (5° F./min). The air flow rate inside the calciner was adjusted at 5 volume/volume catalyst/minute. The nitric acid treated RT-235 silica support is abbreviated as AW-RT-235 (acid washed RT-235).

Example 2—Characterization of Untreated and Acid Treated Silica Supports

The untreated (RT-235) and acid treated (AW-RT-235) silica supports were characterized by their BET surface area (ASTM D1993), median pore size (mercury porosimetry according to ASTM D4284-12), pore volume (mercury porosimetry according to ASTM D4284-12) and crush strength (standard test method for single pellet crush strength of formed catalyst shapes according to ASTM D4179-01). Said RT-235 and AW-RT-235 silica supports were also compared to a conventional silica support sold by PQ Corporation, referred to as PQ $SiO_2$. The results are summarized in Table 1 below.

TABLE 1

| Silica supports | BET surface area (m²/g) | Pore vol (ml/g) | Median pore diameter (nm) | Crush strength (g/mm/lb/in) |
|---|---|---|---|---|
| PQ $SiO_2$ | 205 | 1.1 | 17.4 | — |
| RT-235 $SiO_2$ | 98 | 0.71 | 27.7 | 1733/97.0 |
| AW-RT-235 $SiO_2$ | 96 | 0.88 | 29.3 | 1590/89.0 |

It can be seen from Table 1 that RT-235 silica support has a lower surface area and a larger pore size compared to conventional silica supports such as PQ silica.

As far as acid treatment of the RT-235 silica support is concerned, it did not substantially alter the BET surface area. Also, the median pore size, the pore volume and the crush strength of the acid treated silica extrudates (AW-RT-235) were comparable to the properties of the untreated RT-235 silica support. For instance, the crush strength changed from 1733 g/mm (97.0 lb/in) to 1590 g/mm (89.0 lb/in), this second value being still highly above 893 g/mm (50 lb/in) which is considered as an acceptable crush strength for an extrudate catalyst in industrial applications.

Example 3—Ru/$SiO_2$ Catalyst Preparation by Ruthenium Impregnation and Calcination Silica-supported ruthenium catalysts were prepared by incipient wetness impregnation. Untreated silica supports (RT-235) and silica supports as treated in Example 1 (AW-RT-235) were used as catalyst supports. The ruthenium precursor compound used in the catalyst preparation was ruthenium nitrosyl nitrate. The chelation aid added in the impregnation solution was triethanolamine (TEA). The mixture solution was prepared by adding appropriate amounts of TEA and ruthenium nitrosyl nitrate into distilled $H_2O$. The volume of the impregnation solution used was about 95% of the solution absorption capacity of the silica support. For example, 8.37 g of ruthenium nitrosyl nitrate solution containing 1.5 wt % Ru was added to 3.73 g of triethanolamine (TEA). 10 g of water was added to the mixture of Ru-TEA. The solution was stirred until it was clear. The total solution volume prepared was about 23.8 ml. The concentration of Ru in the solution was 0.05 M and TEA was 1.05 M. The molar ratio of TEA to Ru was 21.25 g of silica supports was used in the catalyst preparation. After deposition of the ruthenium on the silica supports, the ruthenium-containing silica supports were dried in air at 100° C. for 12 hours and calcined in air at 275° C. for 1 hour with a ramping rate of 5° C./min to produce a silica-supported ruthenium catalyst. The air flow rate inside the calciner was adjusted at 5 volume/volume catalyst/minute. The silica-supported ruthenium catalysts contained 0.5% Ru metal, with respect to the total weight of catalyst.

Example 4—Activation of the Ru/SiO$_2$ Catalysts by Reduction and Passivation

The reduction reactor was ramped from room temperature to 425° C. at 5° C./min rate. The silica-supported ruthenium samples prepared according to Example 3 were reduced at 425° C. for 2.5 hours with 100% hydrogen. The hydrogen pressure was 34 kPa gauge (5 psig) adjusted by backpressure regulator plus atmospheric pressure. The reduced catalysts were allowed to cool down to room temperature in a H$_2$ flow. When the temperature of the reactor reached room temperature, the H$_2$ flow was replaced with a mixture of 1% air balanced with N$_2$. The catalyst passivation was carried out at room temperature for 2 hrs. The gas flow of 1% air/N$_2$ then was adjusted at 5 volume/volume catalyst/minute.

Example 5—Hydrogen Chemisorption and Elemental Analysis

A Micromeritics ASAP 2020 Chemi system was used to measure the hydrogen chemisorption and calculate the Ru dispersion of the silica-supported ruthenium catalysts prepared according to Example 3. The silica-supported ruthenium hydrogenation catalyst samples were dried under helium at 20° C. for 30 minutes to remove any moisture. Sample reduction was carried out at 200° C. in hydrogen for 30 minutes. The ramping rate was controlled at 5° C./min. After reduction, the sample chamber was evacuated at 200° C. for 1 hour, then the reactor was cooled down to room temperature while the system was still under vacuum. The hydrogen isothermal was measured at room temperature. The H/Ru chemisorption ratio was calculated by extrapolation of the isothermal profile to zero hydrogen pressure.

The residual carbon and nitrogen contents of the silica-supported ruthenium catalysts of Example 3 were determined by chemiluminescence. The ruthenium and sodium contents of the catalysts were determined by X-ray fluorescence (XRF).

The results of the hydrogen chemisorption and elemental analysis are summarized in Table 2 below.

TABLE 2

| Catalyst supports | C and N (%) | Ru and Na (%) | H/Ru chemisorption ratio |
|---|---|---|---|
| RT-235 | C: 2.8 N: 1.0 | Ru: 0.53 Na: 0.19 | 0.39 |
| AW-RT-235 | C: 2.9 N: 1.1 | Ru: 0.54 Na: 0.10 | 0.81 |

The results of Table 2 show residual carbon and nitrogen contents of respectively 2.8-2.9% and 1.0-1.1% for both untreated (RT-235) and acid treated (AW-RT-235) supported catalysts, even after calcination at 275° C. in air for 1 hour according to the procedure of Example 3. Said carbon and nitrogen residue contents indicate the formation of organic remnants after partial decomposition of Ru-TEA complexes during said calcination step.

The results of Table 2 also show that the ruthenium dispersion on the AW-RT-235 support was greatly increased compared to the untreated RT-235 silica support, with a H/Ru chemisorption ratio of 0.81 compared to 0.39. The hydroxyl groups of the silica support are the anchoring points for the ruthenium. Without being bound by any theory, it is believed that the higher Ru dispersion on the silica surface, as shown by the higher H/Ru chemisorption ratio, results from a higher concentration of hydroxyl groups on the treated silica support, brought by the acid treatment. Said higher Ru dispersion will thus generate more active sites for phthalate hydrogenation.

Also, the XRF elemental analysis indicated that, after nitric acid treatment, the sodium content of the AW-RT-235 supported catalyst was decreased to 0.10%, compared to 0.19% for the untreated RT-235 supported catalyst.

Example 6—Catalyst Activity Evaluation for the Hydrogenation of Diisononylphthalate (DINP)

The AW-RT-235 supported catalyst prepared in Example 3, containing 0.5 wt % Ru, was tested for the hydrogenation of diisononylphthalate (DINP) according to the process described below. Said catalyst was compared to reference catalysts containing 0.5 wt % Ru dispersed on various commercial silica supports. These reference catalysts were prepared in a similar way to Example 3, i.e., by impregnation of the silica supports with ruthenium nitrosyl nitrate in the presence of triethanolamine, followed by drying and calcination.

2 g of silica-supported ruthenium hydrogenation catalyst, containing 0.5% Ru, were activated in a fixed bed reactor for 19 hours at 200° C. under 80 bar pressure of H$_2$. The H$_2$ gas flow rate was adjusted at 30 ml/min. The feed used for the catalyst evaluation was a blend of 50 wt % diisononyl phthalate (DINP) balanced with 50% isoparaffins (Isopar C). The liquid feed flow rate was adjusted to ensure 40-80% DINP conversion (i.e., WHSV 2.5 h$^1$, or 10 g feed/h, or 5 g DINP/h). For this liquid flow rate, the hydrogen flow rate was set at 20 ml/min. In case the WHSV changed, the hydrogen flow rate was adjusted accordingly to maintain the same DINP/hydrogen flow ratio. The system pressure was maintained at 80 bar H$_2$. The temperature of the reactor was set at 80° C. The run was continued till the steady state conversion was obtained at 80° C. The reaction products were analyzed offline by gas chromatography (GC) and near infra-red (IR).

The catalyst activities were evaluated by comparing the 1st order rate constant (k) per mol Ru for the DINP disappearance.

$\ln [DINP] = -k.t + \ln [DINP]_o$

The results are summarized in Table 3 below.

TABLE 3

| Catalysts | Activity |
|---|---|
| AW-RT-235 support | 9000 |
| Commercial Fumed SiO$_2$ | 5000 |
| Commercial SiO$_2$ spheres | 3500 |
| Commercial SiO$_2$ gel | 3000 |
| Commercial SiO$_2$ | 3000 |
| Commercial SiO$_2$ | 2000 |
| Commercial SiO$_2$ | 2000 |

Table 3 shows that the catalyst based on AW-RT-235 was by far the most active amongst the various tested catalyst examples.

The present invention has been described and illustrated by reference to particular embodiments. Those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for the preparation of a silica-supported noble metal hydrogenation catalyst comprising the steps of:
   (a0) steam treating a silica material to obtain a steam-treated silica support having a median pore size of at least about 10 nm and no more than about 300 nm and a silica content of at least 60 wt %;
   (a) contacting the steam-treated silica support with an acid to make an acid-treated silica support, thereafter calcining the acid-treated silica support at a temperature in the range of from about 250° C. to about 1000° C. to obtain a calcined silica support; and
   (b) contacting the calcined silica support obtained in step (a) with a solution comprising a noble metal salt and a chelating agent to produce a noble metal-containing silica support, wherein the chelating agent has at least one carboxylic acid functional group or hydroxyl functional group and from 2 to 20 carbon atoms.

2. The method of claim 1, wherein the noble metal is selected from the group consisting of ruthenium, rhodium, palladium, platinum and mixtures thereof.

3. The method of claim 1, wherein the noble metal is ruthenium.

4. The method of claim 1, further comprising the step of calcining the noble metal-containing silica support obtained in step (b).

5. The method of claim 1, wherein the noble metal-containing silica support has a hydrogen to noble metal chemisorption ratio of at least about 0.50.

6. The method of claim 1, wherein the silica support used in step (a) has a median pore size of at least about 20 nm.

7. The method of claim 1, wherein the hydroxyl group concentration of the surface of the acid-treated silica support obtained in step (a) is at least 1 Si—OH group per $nm^2$ greater than that of the silica support used in step (a).

8. The method of claim 1, wherein the acid used in step (a) is in the form of an aqueous solution having a pH of from about 0.0 to about +3.0.

9. The method of claim 1, wherein the acid used in step (a) is nitric acid.

10. The method of claim 1, wherein the steam-treated silica support used in step (a) has a crush strength of at least 800 g/mm.

11. The method of claim 1, further comprising the step of activating the catalyst by contacting the noble metal-containing silica support obtained in step (b) with hydrogen gas.

12. The method of claim 1, wherein the steam-treated silica support has a silica content of at least 80 wt %.

13. The method of claim 1, wherein in step (a0), the silica material is steam treated at a temperature of at least 400° C.

14. The method of claim 1, wherein in step (a0), the silica material is steam treated at a temperature in a range from about 500° C. to about 800° C.

* * * * *